(12) United States Patent  
Algawi et al.

(10) Patent No.: US 11,723,517 B2  
(45) Date of Patent: Aug. 15, 2023

(54) WIRING OF TROCAR HAVING MOVABLE CAMERA AND FIXED POSITION SENSOR

(71) Applicant: BIOSENSE WEBSTER (ISRAEL) LTD., Yokneam (IL)

(72) Inventors: Yehuda Algawi, Binyamina (IL); Assaf Govari, Haifa (IL); Ilya Sitnitsky, Nahariya (IL); Gili Attias, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 341 days.

(21) Appl. No.: 16/731,494

(22) Filed: Dec. 31, 2019

(65) Prior Publication Data

US 2021/0196105 A1   Jul. 1, 2021

(51) Int. Cl.
*A61B 1/00*   (2006.01)
*A61B 1/05*   (2006.01)
(Continued)

(52) U.S. Cl.
CPC ...... *A61B 1/00064* (2013.01); *A61B 1/00045* (2013.01); *A61B 1/00066* (2013.01);
(Continued)

(58) Field of Classification Search
CPC ............ A61B 1/00154; A61B 1/00039; A61B 1/00066; A61B 1/00124; A61B 1/00128; A61B 1/053; A61B 1/0684; A61B 1/313; A61B 5/062; A61B 5/066; A61B 17/3423; A61B 17/3421; A61B 90/361;
(Continued)

(56) References Cited

U.S. PATENT DOCUMENTS 5,391,199 A   2/1995   Ben-Haim  
6,063,022 A * 5/2000  Ben-Haim ............ A61B 5/287  
                                      600/41

(Continued)

FOREIGN PATENT DOCUMENTS

EP   3108795    12/2016  
EP   3510963    7/2019  
WO   WO9605768  2/1996

OTHER PUBLICATIONS

International Search Report dated Apr. 14, 2021 from corresponding PCT Patent Application No. PCT/IB2020/061945.

*Primary Examiner* — Anh Tuan T Nguyen  
*Assistant Examiner* — Sung Ham  
(74) *Attorney, Agent, or Firm* — Frost Brown Todd LLP

(57) ABSTRACT

A medical apparatus includes a trocar, a control handle, a first electrical wire, and a second electrical wire. The trocar is used for insertion into an organ of a patient, and includes (i) a cannula having a longitudinal axis, (ii) a position sensor that is fitted inside the cannula, and (iii) a camera that is coupled to a movable element, which is fitted inside the cannula and configured to be moved along the longitudinal axis for moving the camera along the cannula. The control handle is coupled to a proximal end of the movable element and is configured to move the movable element and the camera. The first electrical wire is coupled between the control handle and the camera. The second electrical wire is coupled between the control handle and the position sensor, and has a slack configured to compensate for a motion of the camera.

21 Claims, 3 Drawing Sheets

(51) Int. Cl.
   *A61B 1/06* (2006.01)
   *A61B 1/313* (2006.01)
   *A61B 5/06* (2006.01)
   *A61B 17/34* (2006.01)

(52) U.S. Cl.
   CPC ...... *A61B 1/00124* (2013.01); *A61B 1/00128* (2013.01); *A61B 1/00154* (2013.01); *A61B 1/053* (2013.01); *A61B 1/0684* (2013.01); *A61B 1/313* (2013.01); *A61B 5/062* (2013.01); *A61B 5/066* (2013.01); *A61B 17/3423* (2013.01)

(58) Field of Classification Search
   CPC ............ A61B 1/00114; A61B 1/00064; A61B 2034/2051; A61B 17/34; A61B 17/3417; A61B 2017/3405; A61B 2017/3454
   See application file for complete search history.

(56) References Cited

U.S. PATENT DOCUMENTS

| | | | |
|---|---|---|---|
| 6,239,724 B1 | 5/2001 | Doron et al. | |
| 6,332,089 B1 | 12/2001 | Acker et al. | |
| 6,447,504 B1* | 9/2002 | Ben-Haim | A61B 34/20 606/15 |
| 6,484,118 B1 | 11/2002 | Govari | |
| 6,618,612 B1 | 9/2003 | Acker et al. | |
| 6,643,538 B1* | 11/2003 | Majewski | A61B 6/4258 600/113 |
| 6,690,963 B2 | 2/2004 | Ben-Haim et al. | |
| 7,881,769 B2* | 2/2011 | Sobe | A61B 34/20 600/424 |
| 2002/0010479 A1 | 1/2002 | Skakoon et al. | |
| 2002/0065455 A1 | 5/2002 | Ben-Haim et al. | |
| 2002/0143236 A1 | 10/2002 | Sauer et al. | |
| 2003/0050598 A1* | 3/2003 | Hayzelden | A61M 25/0147 604/95.04 |
| 2003/0120150 A1 | 6/2003 | Govari | |
| 2004/0068178 A1 | 4/2004 | Govari | |
| 2005/0027195 A1* | 2/2005 | Govari | A61B 5/065 600/433 |
| 2006/0025651 A1* | 2/2006 | Adler | A61B 1/0011 600/110 |
| 2006/0074289 A1* | 4/2006 | Adler | A61B 1/0005 600/407 |
| 2007/0106156 A1* | 5/2007 | Altmann | A61B 34/20 600/437 |
| 2007/0198007 A1* | 8/2007 | Govari | A61B 34/20 606/41 |
| 2009/0221907 A1* | 9/2009 | Bar-Tai | A61B 5/064 600/424 |
| 2010/0081875 A1* | 4/2010 | Fowler | A61B 1/00188 600/114 |
| 2010/0152533 A1 | 6/2010 | Mark | |
| 2010/0249817 A1 | 9/2010 | Mark | |
| 2015/0031977 A1* | 1/2015 | Gorhan | A61B 5/283 600/377 |
| 2015/0272617 A1* | 10/2015 | MacDonald | A61B 1/00183 600/110 |
| 2016/0234408 A1* | 8/2016 | Urakawa | G02B 23/2476 |
| 2016/0310042 A1* | 10/2016 | Kesten | A61B 34/20 |
| 2018/0263477 A1* | 9/2018 | Aoki | A61B 1/045 |
| 2018/0344978 A1* | 12/2018 | Shameli | A61B 17/24 |
| 2019/0335987 A1* | 11/2019 | Cook | A61B 1/00105 |
| 2020/0022572 A1* | 1/2020 | Mathonnet | A61B 17/00008 |
| 2020/0107714 A1* | 4/2020 | Bar-Or | A61B 90/361 |
| 2020/0221927 A1* | 7/2020 | Matthison-Hansen | A61B 1/015 |
| 2020/0345414 A1* | 11/2020 | Datta | A61B 34/20 |

* cited by examiner

WIRING OF TROCAR HAVING MOVABLE CAMERA AND FIXED POSITION SENSOR

FIELD OF THE INVENTION

The present invention relates generally to invasive medical tools, and particularly to methods and systems for invasive medical tools incorporating a camera.

BACKGROUND OF THE INVENTION

Various techniques for image-guided probing of a patient organ that are using invasive devices and wiring thereof have been published in the patent literature.

For example, U.S. Patent Application Publication 2010/0152533, issued as U.S. Pat. No. 9,655,639 on May 23, 2017, describes a tissue cutting device that is especially suited for neurosurgical applications. The device includes a handpiece and an outer cannula in which a reciprocating inner cannula is disposed. The inner cannula includes a hinge between a body section and a cutting section that allows the cutting section to pivot when the inner cannula reciprocates within the outer cannula. The tissue cutting device may be used with imaging device such as microscopes and endoscopes during neurosurgery procedures.

U.S. Patent Application Publication 2002/0010479, issued as U.S. Pat. No. 7,660,621 on Feb. 9, 2010, describes an introducer that is coupled to a patient, specifically a patient's skull. The introducer may include an advancer that is remote from the patient, the advancer communicating with the introducer by means of a cable system. The introducer may also include a local position sensor that indicates the position of the primary medical device being introduced. The introducer may also include a frameless reference system that locates the primary medical device relative to a table that the patient is fixed to.

U.S. Patent Application Publication 2002/0143236, issued as U.S. Pat. No. 6,685,630 on Feb. 3, 2004, describes an optical obturator which includes a sleeve having a longitudinal bore between a proximal end and a distal end. The longitudinal bore of the sleeve is configured to receive at least a portion of an endoscope or like image transferring system. An image passing member, such as an optical window is positioned at the distal end of the sleeve and is provided to permit optical images to pass into the longitudinal bore of the sleeve and to permit illumination light to pass to the surgical site. An automatically retracting blade is positioned distal to the image passing member to facilitate penetration of body tissue.

SUMMARY OF THE INVENTION

An embodiment of the present invention that is described herein provides a medical apparatus, including a trocar, a control handle, at least a first electrical wire, and at least a second electrical wire. The trocar is used for insertion into an organ of a patient, the trocar includes (i) a cannula having a longitudinal axis, (ii) a position sensor that is fitted inside the cannula, and (iii) a camera that is coupled to a movable element, which is fitted inside the cannula and configured to be moved along the longitudinal axis for moving the camera along the cannula. The control handle is coupled to a proximal end of the movable element and is configured to move the movable element and the camera. The at least first electrical wire is coupled between the control handle and the camera. The at least second electrical wire is coupled between the control handle and the position sensor, and has a slack configured to compensate for a motion of the camera.

In some embodiments, the control handle is configured to contain the slack of the at least second electrical wire. In other embodiments, the slack of the at least second electrical wire is winded within the control handle. In yet other embodiments, the medical apparatus includes a camera control guide, which is coupled between the movable element and the control handle and is configured to move the movable element using the control handle.

In an embodiment, the at least first electrical wire is threaded through the camera control guide. In another embodiment, the camera control guide is configured to move the camera and the at least first electrical wire as a rigid element. In yet another embodiment, the medical apparatus includes (i) at least an electronic device, which is coupled to the movable element, and (ii) at least a third electrical wire, which is coupled between the control handle and the electronic device, and the third electrical wire is threaded through the camera control guide.

In some embodiments, the control handle includes a knob, which is coupled to the camera control guide and is configured to control an amount of movement of the movable element. In other embodiments, the at least first electrical wire includes two or more first electrical wires, and the medical apparatus includes at least an electronic device, which is coupled to the proximal end of the movable element, and at least one of the first electrical wires is coupled between the control handle and the electronic device. In yet other embodiments, the position sensor is fitted at a distal end of the cannula, and the camera is mounted in a tilted configuration so that the position sensor does not obstruct a field of view of the camera.

There is additionally provided, in accordance with an embodiment of the present invention, a method for producing a medical apparatus. The method includes, providing a trocar for insertion into an organ of a patient. The trocar includes (i) a cannula having a longitudinal axis, a position sensor that is fitted inside the cannula, and (ii) a camera that is coupled to a movable element, which is fitted inside the cannula and is movable along the longitudinal axis for moving the camera along the cannula. A control handle, for moving the movable element and the camera, is coupled to a proximal end of the movable element. At least a first electrical wire, is coupled between the control handle and the camera. At least a second electrical wire having a slack for compensating for a motion of the camera, is coupled between the control handle and the position sensor.

There is further provided, in accordance with an embodiment of the present invention, a method including inserting a trocar into an organ of a patient. The trocar includes (i) a cannula having a longitudinal axis, (ii) a position sensor, fitted at a distal end of the cannula and configured to produce signals indicative of a position of the distal end in the organ, and (iii) a camera, which is configured to acquire images of tissue of the organ, the camera is coupled to a movable element, which is fitted inside the cannula and configured to be moved along the longitudinal axis for moving the camera along the cannula. The movable element and the camera are moved using a control handle, which is coupled to a proximal end of the movable element. At least a first electrical wire is coupled between the control handle and the camera, and at least a second electrical wire is coupled between the control handle and the position sensor, and has a slack for compensating for a motion of the camera. A medical procedure is performed in the organ, using at least one of the signals produced by the position sensor and the images acquired by the camera.

The present invention will be more fully understood from the following detailed description of the embodiments thereof, taken together with the drawings in which:

DETAILED DESCRIPTION OF EMBODIMENTS

Overview

Figure 1:
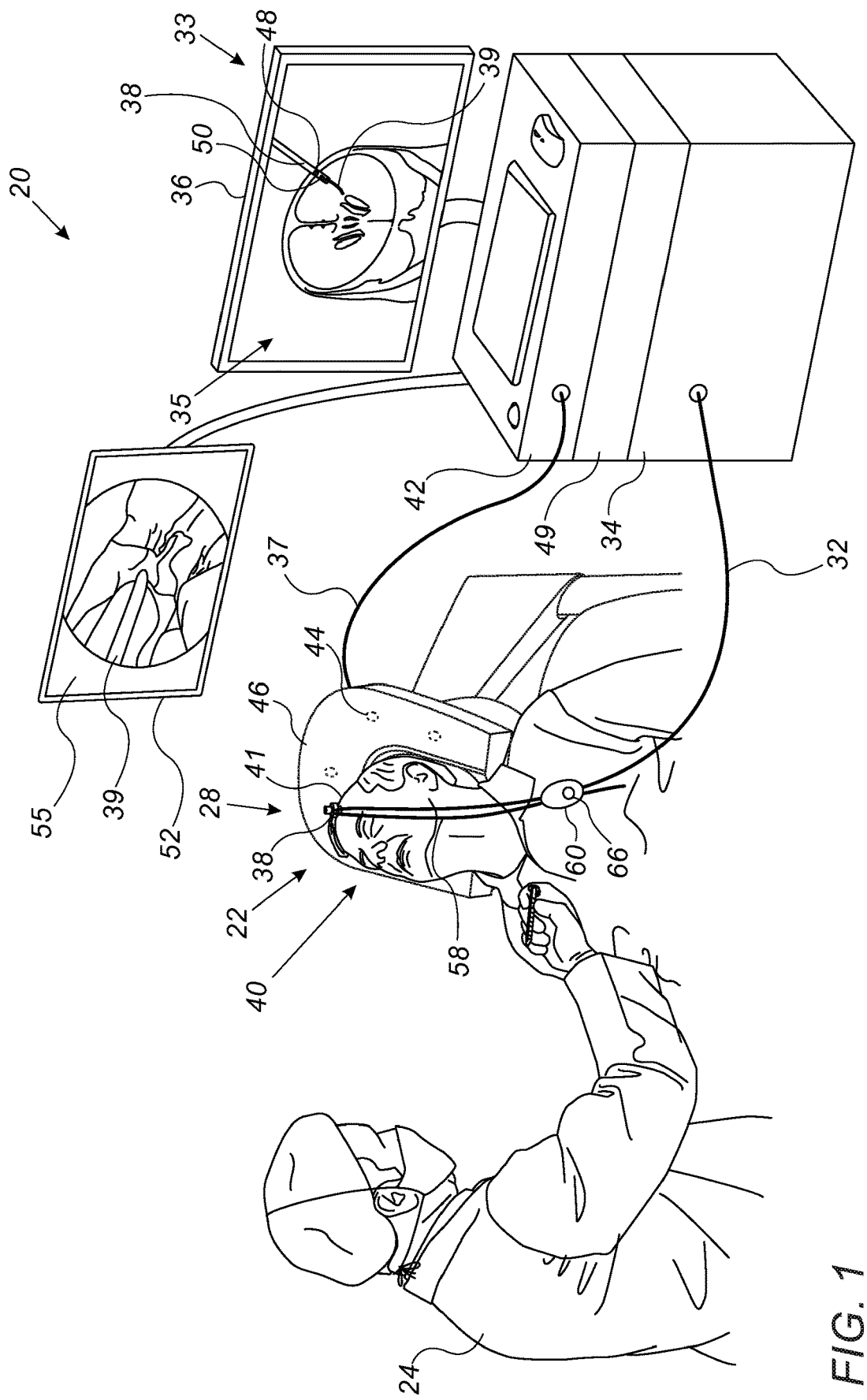
FIG. 1 is a schematic, pictorial illustration of a neurosurgical procedure using a system for performing treatment and diagnostics procedures in a head of a patient, in accordance with an embodiment of the present invention.

Some minimally invasive medical procedures may apply a trocar for inserting diagnostics and/or treatment tools into a target position in a patient organ.

Embodiments of the present invention that are described hereinbelow provide methods and apparatus for improving the functionality of minimally invasive procedures applying a trocar. In some embodiments, a medical apparatus comprises a trocar for insertion into an organ of a patient, e.g., patient head.

In some embodiments, the trocar is inserted, by a physician, into the patient head so as to serve as a port for inserting medical instruments to carry out a medical procedure in a patient brain.

During the procedure, the physician may need to acquire images of brain tissue. In some embodiments, the trocar comprises a cannula having a longitudinal axis and a position sensor, which is fitted inside the cannula at a predefined position, e.g., at a distal end of the cannula located at a distal end of the trocar. The position sensor is configured to produce position signals indicative of a position of the distal end of the trocar in the patient head.

In some embodiments, the trocar comprises a camera, which is configured to acquire images of tissue in question in the patient brain. The camera is coupled to a movable element, which is fitted inside the cannula. The movable element is configured to be moved along the longitudinal axis for moving the camera along the cannula.

In some embodiments, the medical apparatus comprises a control handle, which is coupled to a proximal end of the movable element and is configured to move the movable element and the camera.

In an embodiment, the medical apparatus comprises a camera control guide, which is coupled between the control handle and the movable element. In this embodiment, the camera control guide may serve as the proximal end of the movable element.

In some embodiments, the medical apparatus comprises a first electrical wire, which is coupled between the control handle and the camera, and a second electrical wire, which is coupled between the control handle and the position sensor.

In some cases, the first and second electrical wires are routed through the trocar and may have physical contact with one another, such that when the first electrical wire is moving with the camera, the second electrical wire may be moved due to the physical contact with the first electrical wire. In some embodiments, the second electrical wire has a slack for compensating for the motion of the camera. In such embodiments, the slack allows movement of the second electrical wire without stretching or tearing the second electrical wire.

In some embodiments, the control handle comprises a knob, which is configured to control the amount of movement of the camera. In such embodiments, the knob controls the distance between the camera and the tissue in question, so as to improve the quality of one or more images acquired from the tissue in question.

The disclosed techniques improve the position tracking and image quality obtained in invasive procedures using a trocar, by enabling a combination of a static position sensor and a movable camera incorporated in a single trocar.

System Description

FIG. 1 is a schematic, pictorial illustration of a neurosurgical procedure using a system 20, in accordance with an embodiment of the present invention. In some embodiments, system 20 is configured for performing treatment and diagnostics procedures in a head 41 of a patient 22.

In some embodiments, system 20 comprises a medical apparatus, in the present example a surgical apparatus 28, which is configured to carry out the neurosurgical procedure, also referred to herein a brain procedure, such as but not limited to removing an infection or cancerous tissue from the brain of patient 22.

Figure 2:
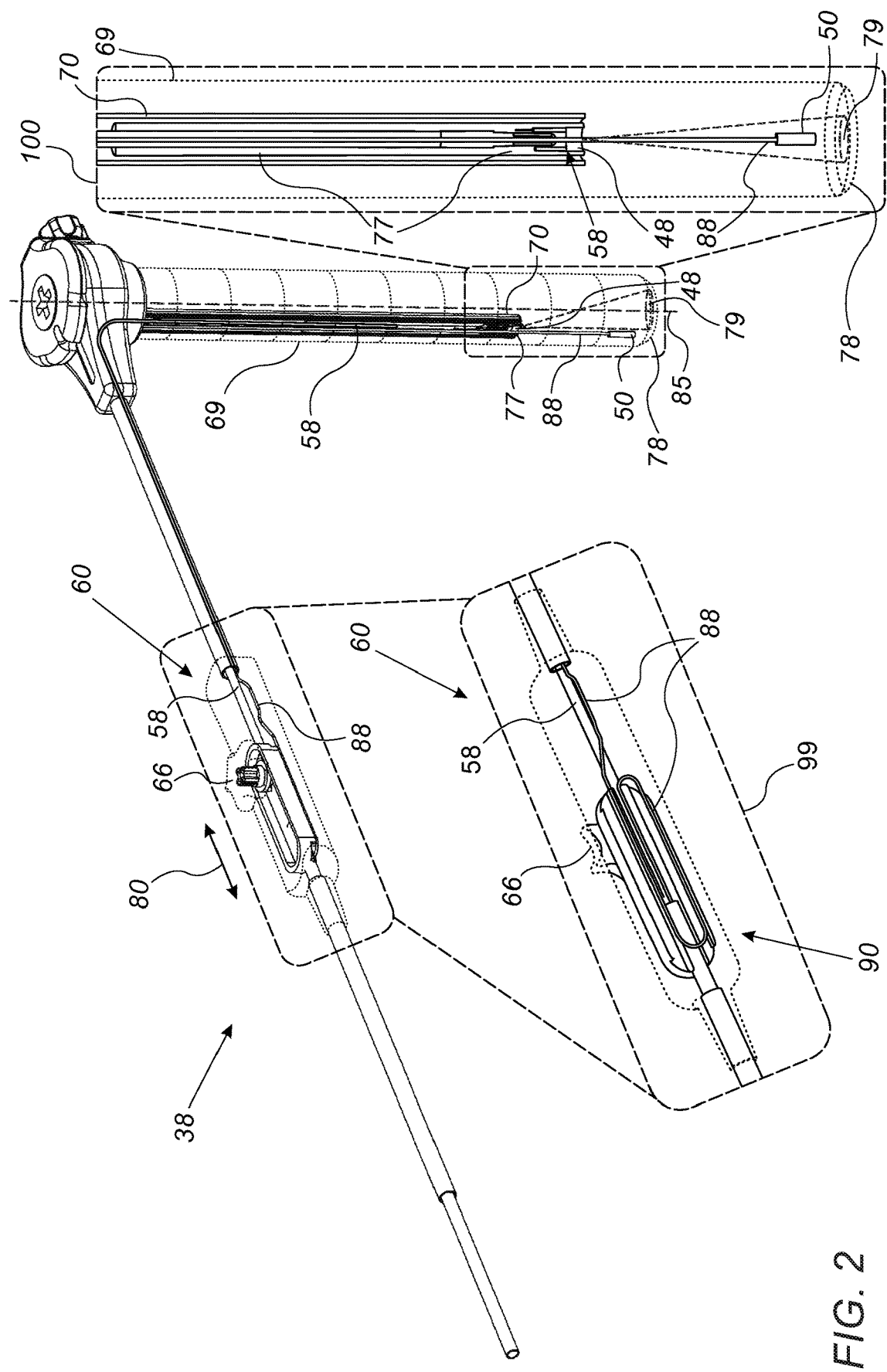
FIG. 2 is a schematic, pictorial illustration of a trocar used in a neurosurgical procedure, in accordance with an embodiment of the present invention.

In some embodiments, surgical apparatus 28 comprises a trocar 38, having a camera 48 that is slidable along trocar 38 as will be described below, and is configured to acquire images at the position of the distal end of trocar 38. Trocar further comprises a position sensor 50 of a position tracking system, which is configured to produce position signals indicative of the position of position sensor 50. Camera 48 and position sensor 50 are shown in FIG. 2 below and the respective positions thereof are displayed in FIG. 1, on a display 36 of system 20.

During the procedure, a physician 24 or any other user of system 20, applies trocar 38 for penetrating the skull of patient 22, and subsequently, for inserting a medical instrument, such as a probe 39, through trocar 38, into the brain tissue so as to carry out the procedure. In some embodiments, physician 24 may use the images acquired by camera 48 and the position signals received from position sensor 50, for positioning the distal end of trocar 38 and for operating probe 39 at a target location within the brain. In some cases, probe 39 may be operated by a second physician (not shown).

In some embodiments, system 20 comprises a control handle 60 having a knob 66, which is configured to move camera along trocar 38 and to control the position of the camera within a cannula of trocar 38, as will be described in detail in FIG. 2 below.

In some embodiments, system 20 comprises a camera control guide 58, which enters at a proximal end of trocar 38 and is coupled on to a movable element (not shown) configured to move camera 48 within trocar 38. In some embodiments, physician 24 may rotate knob 66 for sliding camera 48 inside trocar 38 along a longitudinal axis thereof (shown in FIG. 2 below), so as to adjust the position of camera 48 for obtaining a best view of the tissue in question, as further described in FIG. 2.

In some embodiments, system 20 comprises at least two sets of one or more electrical wires (not shown). The first set of electrical wires is coupled between control handle 60 and position sensor 50, and the second set of one or more electrical wires is coupled between control handle 60 and camera 48.

In some embodiments, system 20 comprises additional control elements for assisting physician 24 in performing the procedure, such as command buttons to capture an image from camera 48 and to register the captured image with a reference medical image.

In some embodiment, the aforementioned position tracking system may comprise a magnetic position-tracking system, which is configured to track the position of sensor 50 in the brain. The magnetic position-tracking system comprises a location pad 40, which comprises field generators 44 fixed on a frame 46 and configured to produce magnetic fields sensed by position sensor 50. In the exemplary configuration shown in FIG. 1, pad 40 comprises five field generators 44, but may alternatively comprise any other suitable number of generators 44. Pad 40 further comprises a pillow (not shown) placed under head 41 of patient 22, such that generators 44 are located at fixed, known positions external to head 41.

In some embodiments, position sensor 50 generates position signals in response to sensing the magnetic fields generated by field generators 44, thereby enabling a processor to estimate the position of sensor 50 and therefore a position of a distal edge of trocar 38 inside head 41 of patient 22.

This technique of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, published as U.S. Pat. No. 6,690,963 on Feb. 10, 2004; 2003/0120150 A1, published as U.S. Pat. No. 7,729,742 on Jun. 1, 2010 and 2004/0068178 A1, now abandoned; whose disclosures, in their entirety, are all incorporated herein by reference into this application.

In some embodiments, system 20 comprises a console 33, which comprises a memory 49, and a driver circuit 42 configured to drive field generators 44, via a cable 37, with suitable signals so as to generate magnetic fields in a predefined working volume in space around head 41.

Processor 34 is typically a general-purpose computer, with suitable front end and interface circuits for receiving images from camera 48 and signals from position sensor 50 via a cable 32, and for controlling other components of system 20 described herein.

In some embodiments, processor 34 is configured to receive an anatomical image of at least part of head 41, which is typically acquired using a medical imaging system, such as but not limited to a magnetic resonance imaging (MRI) system. Processor 34 is configured to select a two-dimensional (2D) slice of the anatomical image, and to display the 2D slice as an image 35 on display 36.

In some embodiments, processor 34 is configured to register between the coordinate systems of image 35 and the magnetic position-tracking system, and to overlay the position of position sensor 50 on image 35.

In some embodiments, console 33 comprises a video display 52 configured for displaying an image 55 acquired by camera 48 and processed by processor 34. In the example of FIG. 1, image 55 shows a distal end of probe 39 engaging brain tissue of patient 22.

In some embodiments, processor 34 is further configured to display on display 52, the position of the distal end of trocar 38 overlaid on image 55, using the position signals received from position sensor 50. Processor 34 is further configured to register the camera image and the anatomical image with the coordinate system of the magnetic position-tracking system and/or in a coordinate system of image 35.

In some embodiments, processor 34 is configured to register a selected 2D slice of the anatomical image, with a real-time camera image, such as image 55, and to produce a combined image and to display the combined image on display 36 and/or on display 52. In the example of FIG. 1, combined image 35 depicts a sectional coronal view of anterior brain tissue of patient 22.

In some embodiments, console 33 further comprises input devices, such as a keyboard and a mouse, for controlling the operation of console 33. Display 36 is configured to display at the same time, at least one of the aforementioned images and the inputs received inserted by a user (e.g., physician 24) operating the input devices.

FIG. 1 shows only elements related to the disclosed techniques for the sake of simplicity and clarity. System 20 typically comprises additional or alternative modules and elements that are not directly related to the disclosed techniques, and thus are intentionally omitted from FIG. 1 and from the corresponding description. In alternative embodiments, knob 66 of control handle 60 may comprise a slider button instead of, or in addition to, a rotatable knob shown in detail in FIG. 2 below.

In some embodiments, processor 34 may be programmed in software to carry out the functions that are used by the system, and to store data in memory 49 to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

Trocar with Slidable Camera and Built-in Position Sensor

FIG. 2 is a schematic, pictorial illustration of trocar 38 used in the procedure of FIG. 1, in accordance with an embodiment of the present invention. In some embodiments, trocar 38 has a cannula 69, comprising a channel 70 along a longitudinal axis 85 of trocar 38. Channel 70 serves as a track for sliding camera control guide 58 along longitudinal axis 85.

In some embodiments, camera 48 is coupled to a movable element 77, also referred to herein as a sliding adapter, which is configured to be moved by camera control guide 58 inside cannula 69. In such embodiments, movable element 77 is configured to move camera 48 distally and proximally, along longitudinal axis 85, inside cannula 69.

In some embodiments, physician 24 rotates knob 66 of control handle 60 in a first direction (e.g., clockwise) so as to slide camera control guide 58 distally. In the example configuration of FIG. 2, knob 66 is coupled to a gear that moves, in response to the knob rotation, back or forth along a direction 80. As shown in FIG. 2, the rotation of knob 66 moves knob 66 together with camera control guide 58 forward, so that knob 66 is positioned at the distalmost position within control handle 60. This position is translated (e.g., by the approximately right angle turning of camera control guide 58) into a motion of camera 48 distally inside cannula 69, such that movable element 77 and camera 48 are positioned at the distalmost position within cannula 69.

Similarly, physician 24 may rotate knob 66 in an opposite direction (e.g., counterclockwise), such that knob 66 is moved toward the distal end of control handle 60. In this configuration, control handle 60 pull camera control guide 58 toward the proximal end of trocar 38, which is translated into a motion of camera 48 proximally inside cannula 69.

In some embodiments, position sensor 50 is fixed to an inner wall of cannula 69, and is electrically coupled to control handle 60 via one or more electrical wires 88. In such embodiments, the position signals produced by position sensor 50 are sent to processor 34 via wires 88 and cable 32 described in FIG. 1 above.

In some embodiments, trocar 38 comprises one or more electrical wires for electrically coupling between control handle 60 and camera 48. In some embodiments, camera 48 is mounted in a tilted configuration so as to have a central distal viewing direction pointing at a center of an opening 78 at the distal end of cannula 69. Note that position sensor 50 is sufficiently small and is attached to the wall of cannula 69, such that position sensor 50 does not obstruct a field of view 79 of camera 48.

In some embodiments, trocar 38 may comprise electronic devices (not shown), such as but not limited to light emitting diodes (LEDs). The LEDs are coupled to movable element 77, e.g., in close proximity to camera 48, and are configured to illuminate the tissue in question during the neurosurgical procedure. In such embodiments, trocar 38 comprises one or more electrical wires coupling between the electronic devices and control handle 60. In the example configuration of trocar 38, the electrical wires that are coupling between control handle 60 and (i) camera 48 and/or (ii) the LEDs, are threaded within camera control guide 58 and are therefore not shown.

In such embodiments, camera control guide 58 and the electrical wires coupled to camera 48 and to the LEDs are moving as a rigid body in response to the rotation of knob 66 by physician 24.

Reference is now made to an inset 100 showing a sectional view of the distal end of trocar 38 from a perspective different than that of the general view of FIG. 2. In some embodiments, position sensor 50 is fitted at a distal end of cannula 69.

Reference is now made back to the general view of FIG. 2. In some embodiments, one or more electrical wires 88 that are coupled to position sensor 50, are threaded within trocar 38, but are not inserted into camera control guide 58, because position sensor 50 is fitted inside cannula 69 (e.g., coupled to the wall thereof) without being moved along longitudinal axis 85. Note that when camera control guide 58 moves within trocar 38, one or more electrical wires 88 may be moved to some extent, for example, due to a friction induced by the motion of camera control guide 58.

Reference is now made to an inset 99 showing a bottom view of control handle 60. In some embodiments, electrical wires 88 have a slack 90, so as to prevent damage to electrical wires 88 when camera control guide 58 is moving. For example, slack 90 may prevent stretching and/or tearing of one or more electrical wires 88 in response to the motion of camera control guide 58. In such embodiments, when camera control guide 58 is moved by knob 66, slack 90 allows some motion of electrical wires 88 (caused by the aforementioned friction) with camera control guide 58, without having an excess tensile force applied to electrical wires 88.

In some embodiments, control handle 60 is configured to contain slack 90, so that no loose section of one or more electrical wires 88 may undesirably be winded around camera control guide 58 and/or knob 66 and/or any other part of trocar 38.

In other embodiments, trocar 38 may have any other suitable mechanism to retain slack 90 within a predefined volume other than within control handle 60.

In some embodiments, during the medical procedure physician 24 inserts trocar 38 into head 41, or any other organ in question, of patient 22. Processor 34 displays the position of position sensor 50 in head 41 so as to assist physician 24 with positioning opening 78 at the target location within head 41. Note that at any stage of the procedure, physician 24 may apply camera 48 for acquiring images, such as image 55, or video clips of the brain tissue of patient 22.

In some embodiments, physician 24 may move movable element 77 and camera 48 using knob 66 of control handle 60, which is coupled to the proximal end of movable element 77. After positioning opening 78 at the target location within head 41, physician 24 may insert, through trocar 38, one or more medical instruments, such as probe 39, so as to perform the medical procedure. Note that processor 34 may use position signals, from position sensor 50 and/or from additional position sensors coupled, for example, to the distal end of probe 39, for displaying the respective positions of the distal ends of trocar 38 and probe 39 for assisting physician 24 to carry out the procedure.

In some embodiments, physician 24 may use the aforementioned images and/or video clips acquired by camera 48 and displayed by processor 34, for performing the medical procedure.

The configuration of trocar 38 in FIG. 2 is depicted by way of example for the sake of conceptual clarity. In other embodiments, additional elements may be included, such as additional ports in trocar 38 to insert medical tools to the target brain location.

Figure 3:
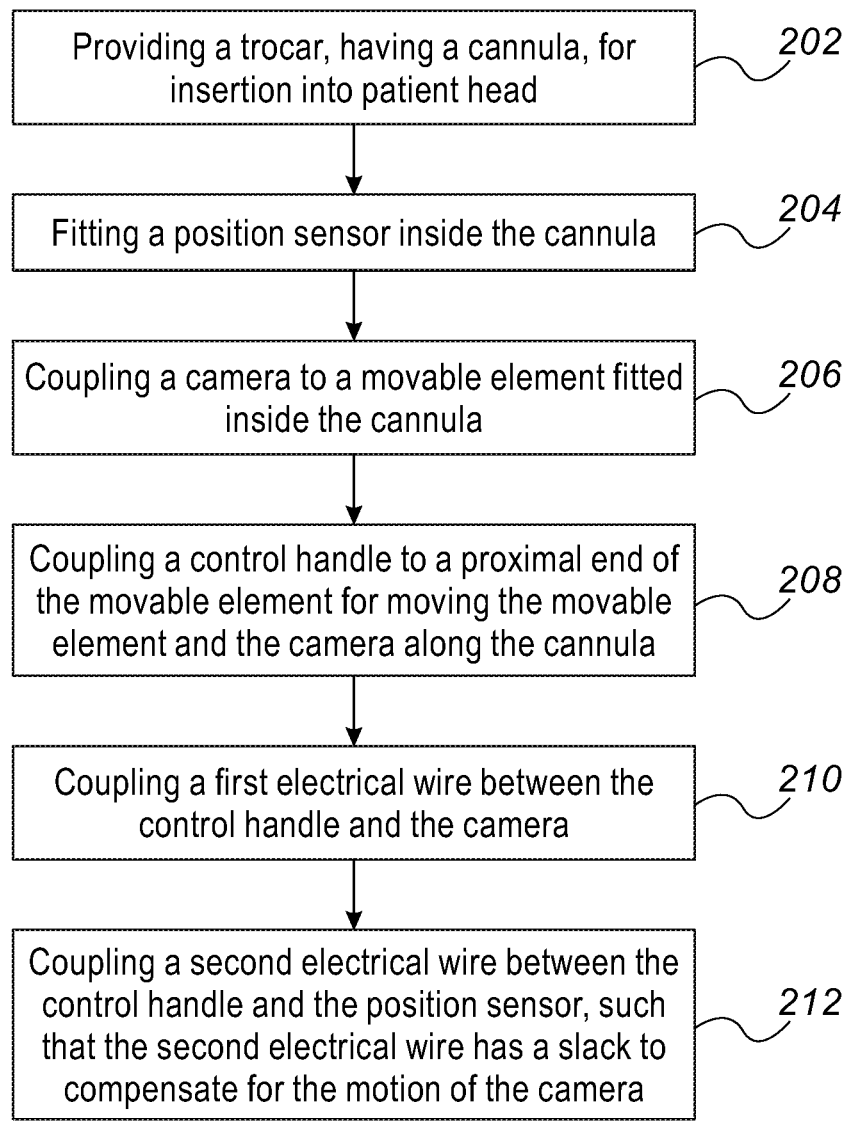
FIG. 3 is a flow chart that schematically illustrates a method for producing a trocar having a movable camera and a static position sensor, in accordance with an embodiment of the present invention.

FIG. 3 is a flow chart that schematically illustrates a method for producing trocar 38 having movable camera 48 and static position sensor 50, in accordance with an embodiment of the present invention. The method begins at a trocar providing step 202 with providing trocar 63 for insertion into patient head 41, wherein trocar 63 has cannula 69 as described in FIG. 2 above.

At a position sensor fitting step 204, position sensor 50 is fitted inside cannula 69. Note that in the example of trocar 38, position sensor 50 is coupled to an inner wall of cannula 69, but in other embodiments, position sensor 50 may be coupled to any other suitable element of trocar 38 and remained static at the coupling location.

At a camera coupling step 206, camera 48 is coupled to movable element 77, which is fitted inside cannula 69 and is coupled to camera control guide 58. In this configuration, movable element 77 is configured to be moved together with camera 48, by camera control guide 58 as described in FIG. 2 above.

At a control handle coupling step 208, control handle 60 is coupled to the proximal end of movable element 77 so that physician 24 may apply control handle 60 for moving movable element 77 and camera along longitudinal axis 85 of cannula 69.

At a first electrical wire coupling step 210, one or more electrical wires are coupled between control handle 60 and camera 48. As described in FIG. 2 above, these electrical wires are threaded into camera control guide 58, and therefore, are not shown in FIG. 2. Note that camera control guide 58 is moved, by knob 66 of control handle 60, as a rigid element together with camera 48 and movable element 77.

At a second electrical wire coupling step 212, one or more electrical wires 88 are coupled between control handle 60 and position sensor 50. In some embodiments, electrical wires 88 have a slack to compensate for the motion of camera 48, as described in FIG. 2 above.

In an embodiment, slack 90 is winded within control handle 60 so that no loose section of one or more electrical wires 88 may undesirably be winded around camera control guide 58 and/or any other part of trocar 38, as described in FIG. 2 above.

In some embodiments, electrical wire coupling step 212 concludes the method of FIG. 3. In other embodiments, the order of step 202-212 may differ from the order shown in FIG. 3. For example, at least one of electrical wire coupling steps 210 and 212 may be carried out before control handling coupling step 208.

Moreover, the method steps of FIG. 3 are simplified for the sake of conceptual clarity, and the full production process of trocar 38 may comprise additional and/or alternative steps.

Although the embodiments described herein mainly address neurosurgical procedures, the methods and systems described herein can also be used in other applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical apparatus, comprising:
    (a) a trocar for insertion into an anatomical structure of a patient, the trocar comprising:
        (i) a cannula having a longitudinal axis;
        (ii) a position sensor, fitted inside the cannula such that the position sensor is fixed against movement relative to the cannula;
        (iii) a camera, coupled to a movable element, which is fitted inside the cannula and configured to be moved along the longitudinal axis for moving the camera along the cannula;
    (b) a control handle, coupled to a proximal end of the movable element and configured to move the movable element and the camera;
    (c) at least a first electrical wire, which is coupled between the control handle and the camera; and
    (d) at least a second electrical wire, which is coupled between the control handle and the position sensor, and has a slack configured to compensate for a motion of the camera while the position sensor and the control handle are stationary relative to each other.

2. The medical apparatus according to claim 1, wherein the control handle is configured to contain the slack of the at least second electrical wire.

3. The medical apparatus according to claim 2, wherein the slack of the at least second electrical wire is winded within the control handle.

4. The medical apparatus according to claim 1, and comprising a camera control guide, which is coupled between the movable element and the control handle and is configured to move the movable element using the control handle.

5. The medical apparatus according to claim 4, wherein the at least first electrical wire is threaded through the camera control guide.

6. The medical apparatus according to claim 4, wherein the camera control guide is configured to move the camera and the at least first electrical wire as a rigid element.

7. The medical apparatus according to claim 4, and comprising (i) at least an electronic device, which is coupled to the movable element, and (ii) at least a third electrical wire, which is coupled between the control handle and the electronic device, and wherein the third electrical wire is threaded through the camera control guide.

8. The medical apparatus according to claim 4, wherein the control handle comprises a knob, which is coupled to the camera control guide and is configured to control an amount of movement of the movable element.

9. The medical apparatus according to claim 1, wherein the at least first electrical wire comprises two or more first electrical wires, and comprising at least an electronic device, which is coupled to the proximal end of the movable element, wherein at least one of the first electrical wires is coupled between the control handle and the electronic device.

10. The medical apparatus according to claim 1, wherein the position sensor is fitted at a distal end of the cannula and wherein the camera is mounted in a tilted configuration so that the position sensor does not obstruct a field of view of the camera.

11. A method for producing a medical apparatus, the method comprising:
    (a) providing a trocar for insertion into an anatomical structure of a patient, the trocar comprising:
        (i) a cannula having a longitudinal axis;
        (ii) a position sensor, fitted inside the cannula such that the position sensor is fixed against movement relative to the cannula; and
        (iii) a camera, coupled to a movable element, which is fitted inside the cannula and is movable along the longitudinal axis for moving the camera along the cannula;
    (b) coupling, to a proximal end of the movable element, a control handle for moving the movable element and the camera;
    (c) coupling, between the control handle and the camera, at least a first electrical wire; and
    (d) coupling, between the control handle and the position sensor, at least a second electrical wire having a slack for compensating for a motion of the camera while the position sensor and the control handle are stationary relative to each other.

12. The method according to claim 11, wherein coupling the at least second electrical wire, comprises containing the slack of the at least second electrical wire within the control handle.

13. The method according to claim 12, wherein containing the slack within the control handle comprises winding the slack of the at least second electrical wire within the control handle.

14. The method according to claim 11, and comprising coupling, between the movable element and the control handle, a camera control guide for moving the movable element using the control handle.

15. The method according to claim 14, wherein coupling the at least first electrical wire comprises threading, the at least first electrical wire, through the camera control guide.

16. The method according to claim 14, wherein the camera control guide is for moving the camera and the at least first electrical wire as a rigid element.

17. The method according to claim 14, and comprising (i) coupling at least an electronic device to the movable element, (ii) coupling, at least a third electrical wire, between the control handle and the electronic device, and (iii) threading the at least third electrical wire through the camera control guide.

18. The method according to claim 14, wherein coupling the camera control guide, comprises coupling, to the camera control guide, a knob of the control handle, for controlling an amount of movement of the movable element.

19. The method according to claim 11, wherein the at least first electrical wire comprises two or more first electrical wires, and comprising coupling at least an electronic device to the movable element, and wherein coupling the at least first electrical wire comprises coupling, at least one of the first electrical wires, between the control handle and the electronic device.

20. The method according to claim 11, wherein the position sensor is fitted at a distal end of the cannula and wherein the camera is mounted in a tilted configuration so that the position sensor does not obstruct a field of view of the camera.

21. A method, comprising:
(a) inserting a trocar into an anatomical structure of a patient, the trocar comprising:
  (i) a cannula having a longitudinal axis;
  (ii) a position sensor, fitted at a distal end of the cannula such that the position sensor is fixed against movement relative to the cannula, and configured to produce signals indicative of a position of the distal end in the anatomical structure; and
  (iii) a camera, which is configured to acquire images of tissue of the anatomical structure, the camera is coupled to a movable element, which is fitted inside the cannula and configured to be moved along the longitudinal axis for moving the camera along the cannula;
(b) moving the movable element and the camera using a control handle, which is coupled to a proximal end of the movable element, wherein,
  (i) at least a first electrical wire is coupled between the control handle and the camera; and
  (ii) at least a second electrical wire is coupled between the control handle and the position sensor, and has a slack for compensating for a motion of the camera while the position sensor and the control handle are stationary relative to each other; and
(c) performing a medical procedure in the anatomical structure, using at least one of the signals produced by the position sensor and the images acquired by the camera.

* * * * *